United States Patent
Shah et al.

(10) Patent No.: US 11,224,657 B2
(45) Date of Patent: *Jan. 18, 2022

(54) ORALLY DISSOLVING MELATONIN FORMULATION WITH ACIDIFYING AGENT THAT RENDERS MELATONIN SOLUBLE IN SALIVA

(71) Applicant: Société des Produits Nestlé S.A., Vevey (CH)

(72) Inventors: Syed M. Shah, Boca Raton, FL (US); Daniel Hassan, Boca Raton, FL (US); Fred Hassan, Boca Raton, FL (US); Patrick Corsino, Boca Raton, FL (US)

(73) Assignee: Société des Produits Nestlé S. A., Vevey (CH)

( * ) Notice: Subject to any disclaimer, the term of this patent is extended or adjusted under 35 U.S.C. 154(b) by 0 days.

This patent is subject to a terminal disclaimer.

(21) Appl. No.: 15/931,029

(22) Filed: May 13, 2020

(65) Prior Publication Data

US 2020/0268886 A1 Aug. 27, 2020

Related U.S. Application Data

(60) Continuation of application No. 16/676,022, filed on Nov. 6, 2019, now Pat. No. 10,960,075, which is a division of application No. 16/009,372, filed on Jun. 15, 2018, now Pat. No. 10,500,280.

(60) Provisional application No. 62/522,473, filed on Jun. 20, 2017.

(51) Int. Cl.
| | |
|---|---|
| *A61K 47/12* | (2006.01) |
| *A61K 9/00* | (2006.01) |
| *A61K 31/4045* | (2006.01) |
| *A61K 9/20* | (2006.01) |
| *A61K 47/38* | (2006.01) |
| *A61K 9/70* | (2006.01) |

(52) U.S. Cl.
CPC .............. *A61K 47/12* (2013.01); *A61K 9/006* (2013.01); *A61K 9/0056* (2013.01); *A61K 9/2013* (2013.01); *A61K 9/2054* (2013.01); *A61K 9/7007* (2013.01); *A61K 31/4045* (2013.01); *A61K 47/38* (2013.01)

(58) Field of Classification Search
CPC ...... A61K 47/12; A61K 9/0056; A61K 9/006; A61K 9/2013; A61K 9/2054; A61K 9/7007; A61K 31/4045; A61K 47/38
See application file for complete search history.

(56) References Cited

U.S. PATENT DOCUMENTS

| | | |
|---|---|---|
| 6,730,330 B2 | 5/2004 | Whittle et al. |
| 7,682,628 B2 | 3/2010 | Singh |
| 10,500,280 B2 | 12/2019 | Shah et al. |
| 2003/0175355 A1 | 9/2003 | Tobyn et al. |
| 2005/0164987 A1 | 7/2005 | Barberich |
| 2006/0292219 A1 | 12/2006 | Pather et al. |
| 2008/0102133 A1* | 5/2008 | Brueck-Scheffler ........................ A61K 31/4439 424/490 |
| 2008/0171085 A1 | 7/2008 | Elnekave et al. |
| 2008/0260823 A1 | 10/2008 | Dillaha |
| 2008/0317863 A1 | 12/2008 | Nystrom et al. |
| 2009/0011015 A1 | 1/2009 | Gardiner et al. |
| 2009/0047347 A1 | 2/2009 | Maggio |
| 2010/0119601 A1 | 5/2010 | McCarty |
| 2010/0215737 A1 | 8/2010 | Coulter |
| 2010/0240724 A1 | 9/2010 | Chang et al. |
| 2011/0092602 A1 | 4/2011 | Laddha et al. |
| 2012/0195968 A1 | 8/2012 | Shah et al. |
| 2012/0213855 A1 | 8/2012 | Agarwal et al. |
| 2012/0315337 A1* | 12/2012 | Shah .................... A61K 9/5073 424/494 |
| 2013/0052234 A1 | 2/2013 | Goldberg et al. |
| 2014/0303227 A1 | 10/2014 | McCarty |
| 2015/0290177 A1 | 10/2015 | Singh |

FOREIGN PATENT DOCUMENTS

| | | | | |
|---|---|---|---|---|
| ES | 2457718 A1 * | 4/2014 | .......... | A61K 9/2027 |
| WO | 2016141069 A1 | 9/2016 | | |

OTHER PUBLICATIONS

English translation of ES 2457718 from EPO (Year: 2021).*
Google search melatonin oral disintegrating—Mar. 25, 2021 (Year: 2021).*
International Search Report dated Oct. 12, 2018 for PCT/US2018/037698.
Tolentino et al.; "Saliva and Tongue Coating pH Before and After Use of Mouthwashes and Relationship with Parameters of Halitosis"; J Appl. Oral Science; vol. 19, No. 2; pp. 90-94; 2011.
Tomar et al.; "Silicified Microcrystalline Cellulose, Modern Co-Processed Excipient for Low Dose Solid Dosage Forms"; European Journal of Biomedical and Pharmaceutical Sciences; vol. 5, Issue 1; pp. 722-731; 2018.
Walker et al.; "The Effect of Variations in pH and Temperature on Stability of Melatonin in Aqueous Solution"; Journal of Pineal Research; vol. 31; pp. 155-158; Oct. 2001.

(Continued)

*Primary Examiner* — Michael P Cohen
(74) *Attorney, Agent, or Firm* — Christopher M. Ramsey; GrayRobinson, P.A.

(57) ABSTRACT

A composition includes a pharmaceutical tablet dosage form configured to disintegrate in oral saliva and maintain a pH of 4 or less within the saliva during the time the dosage form is dissolving therein, the dosage form including a therapeutically effective amount of melatonin in a carrier matrix, a disintegrant, and a sufficient amount of acid to impart the pH to the saliva, the amount of disintegrant being sufficient to cause the dosage form to completely disintegrate in the saliva within ten minutes from contacting the saliva.

30 Claims, No Drawings

(56) References Cited

OTHER PUBLICATIONS

Munoz et al.; "Obtaining Fast Dissolving Disintegrating Tablets With Different Doses of Melatonin"; International Journal of Pharmaceutics; vol. 467, No. 1; pp. 84-89; Apr. 1, 2014.

* cited by examiner

ORALLY DISSOLVING MELATONIN FORMULATION WITH ACIDIFYING AGENT THAT RENDERS MELATONIN SOLUBLE IN SALIVA

CROSS-REFERENCE TO RELATED APPLICATIONS

This is a continuation of application Ser. No. 16/676,022, filed Nov. 6, 2019, which is a divisional of application Ser. No. 16/009,372, filed Jun. 15, 2018, which claims the benefit of priority to U.S. provisional Application No. 62/522,473, filed Jun. 20, 2017. The entire contents of these prior applications are incorporated by reference herein.

FIELD

This relates to the field of orally dissolving pharmaceutical dosage forms and, more particularly, to those containing melatonin.

BACKGROUND

Melatonin is a naturally produced hormone that helps regulate the body's sleep/wake cycles. The amount of melatonin the body produces depends on the time of day. Endogenous melatonin levels start increasing in the evening, peak during the late night hours, and gradually start decreasing in the early morning.

Melatonin is known to have many therapeutic benefits, especially associated with sleep. It has been used to treat sleep problems such as insomnia and jet lag. It has also been used to help patients re-program their circadian clocks to account for changes in light/dark cycles due to time changes. It has also been proposed to act as an antioxidant.

Conventional oral melatonin treatments present several problems. Oral dosage forms have shown low and variable bioavailability. It can take a long time for absorption into the plasma when administered via the gastrointestinal tract. This is partly due to the fact that melatonin must first release from the dosage form, then permeate the walls of gastrointestinal tract before entering the bloodstream.

Orally-dissolving oral dosage forms also exist, but suffer from their own drawbacks. They often provide an unreliably measurable dose of melatonin to the patient. The dose a patient absorbs can vary even when the same product is administered to the same patient or different patients.

BRIEF SUMMARY

The melatonin compositions described here are formulated to deliver melatonin to the mouth where it is absorbed by the body through the oral mucosa. To overcome the high pH of the saliva and tongue, the composition includes an acidifying agent that lowers the pH inside the mouth, which enhances the oral solubility of melatonin. By being more soluble in the mouth, melatonin may more readily pass through the oral mucosa and into the bloodstream. This may make the melatonin dose in the plasma more predictable when compared to convention orally-dissolving melatonin dosage forms.

A first example of the composition includes a pharmaceutical dosage form configured to disintegrate in saliva and maintain a pH of 4 or less within the saliva during the time the dosage form is dissolving therein. The dosage form may include a therapeutically effective amount of melatonin in a carrier matrix, a disintegrant, and a sufficient amount of acid to impart the pH to the saliva. The amount of disintegrant is sufficient to cause the dosage form to completely disintegrate in the saliva within ten minutes from contacting the saliva.

The dosage form of this first example may be at least one of a sublingual tablet, a buccal tablet, and a polymer strip.

When the dosage form of this first example is a buccal or sublingual tablet, it may be at least 20% w/w of the acid.

When the dosage form of this first example is a polymer strip, it may be at least 5% w/w of the acid.

When the dosage form of this first example is a buccal tablet, it may be at least 6% w/w disintegrant.

When the dosage form of this first example is a sublingual tablet, it may be at least 15% w/w disintegrant.

The therapeutically effective amount of melatonin in this first example may be 0.2 mg to 20 mg.

The dosage form of this first example may be a tablet and the carrier matrix includes microcrystalline cellulose as at least 45% w/w of the dosage form, the acid as at least 20% w/w of the dosage form, and the disintegrant as at least 6% w/w of the dosage form.

The acid in this first example may be a carboxylic acid such as citric acid.

In the dosage form of this first example, the amount of disintegrant may be sufficient to cause the dosage form to completely disintegrate in the saliva within 2 minutes from contacting the saliva.

In the dosage form of this first example, the amount of disintegrant may be sufficient to cause the dosage form to completely disintegrate in the saliva within 1 minute from contacting the saliva.

A second example of the composition includes a pharmaceutical dosage form configured to disintegrate in saliva and maintain a pH of 4 or less within the saliva during the time the dosage form is dissolving therein. The dosage form includes 0.2% w/w to 20% w/w melatonin in therapeutically effective amount; a carrier matrix including 45% w/w to 68% w/w filler, and 6% w/w to 20% w/w disintegrant. The amount of disintegrant is sufficient to cause the dosage form to completely disintegrate in the saliva within ten minutes from contacting the saliva. The dosage form also includes 20% w/w to 30% w/w acid. The amount of acid is effective to impart the pH to the saliva.

The dosage form of this second example may be at least one of a sublingual or buccal tablet.

In the dosage form of this second example, the disintegrant may include crospovidone, the filler may include microcrystalline cellulose, and the acid may include citric acid.

When the dosage form of this second example is a sublingual tablet, the disintegrant may be at least 15% w/w of the dosage form.

The therapeutically effective amount of melatonin in this second example may be 0.2 mg to 20 mg.

The acid in this second example may be a carboxylic acid such as citric acid.

In the dosage form of this second example, the amount of disintegrant may be sufficient to cause the dosage form to completely disintegrate in the saliva within 2 minutes from contacting the saliva.

In the dosage form of this second example, the amount of disintegrant may be sufficient to cause the dosage form to completely disintegrate in the saliva within 1 minutes from contacting the saliva.

A third example of the composition includes an oral strip pharmaceutical dosage form configured to disintegrate in saliva and maintain a pH of 4 or less within the saliva during the time the strip is dissolving therein. The dosage form includes 0.2% w/w to 20% w/w melatonin in therapeutically effective amount; a carrier matrix including 45% w/w to 90% w/w water soluble polymer, 1% w/w to 20% w/w plasticizer; and 5% w/w to 20% w/w acid. The amount of acid is effective to impart the pH to the saliva.

In the composition of this third example, the strip has a thickness of 1 mm or less.

In the composition of this third example, dosage form may further include 20% w/w to 30 w/w surfactant.

In the composition of this third example, the water soluble polymer may be 50% w/w to 70% w/w of the dosage form.

In the composition of this third example, the acid may be 8% w/w to 12% w/w of the dosage form.

In the composition of this third example, the acid may be a carboxylic acid such as citric acid.

Any of the first second and third examples of the composition described above may be used in a method of treatment. An example of such a method includes administering a composition comprising a pharmaceutical dosage form to a subject in need thereof. The pharmaceutical dosage form disintegrates in the subject's saliva while maintaining a pH of 4 or less within the saliva during the time the dosage form is dissolving. The dosage form includes a therapeutically effective amount of melatonin in a carrier matrix, a disintegrant, and a sufficient amount of acid to impart the pH to the saliva. The amount of disintegrant is sufficient to cause the dosage form to completely disintegrate in the saliva within ten minutes from contacting the saliva.

The dosage from in this method may be at least one of a sublingual tablet, a buccal tablet, and a polymer strip.

The dosage form in this method may be a buccal or sublingual tablet, which is at least 20% w/w of the acid.

The dosage form in this method may be is a polymer strip, which is at least 5% w/w of the acid.

The dosage form in this method may be a buccal tablet, which is at least 6% w/w disintegrant.

The dosage form in this method may be a sublingual tablet, which is at least 15% w/w disintegrant.

In this method, the therapeutically effective amount of melatonin may be 0.2 mg to 20 mg.

The dosage form in this method may be a tablet and the carrier matrix may include microcrystalline cellulose as at least 45% w/w of the dosage form, the acid as at least 20% w/w of the dosage form, and the disintegrant as at least 6% w/w of the dosage form.

In this method, administering may occur within 30 minutes of the time the subject desires to fall asleep.

In this method, administering may occur at night after the subject has awoken from sleep and desires to fall back asleep.

In this method, the acid may be a carboxylic acid such as citric acid.

In this method, the amount of disintegrant may be sufficient to cause the dosage form to completely disintegrate in the saliva within 2 minutes from contacting the saliva.

In this method, the amount of disintegrant may be sufficient to cause the dosage form to completely disintegrate in the saliva within 1 minute from contacting the saliva.

DESCRIPTION OF EXAMPLE EMBODIMENTS

A problem with administering melatonin via an orally-releasing dosage form is that the pH of the mouth, especially the tongue coating, is too high. The pH of the saliva has been reported to be about 6.4-6.6 and the pH of the tongue coating has been reported to be about 7.1-7.4. See Tollentino et al, *Journal of Applied Oral Science,* 19(2), pg. 90 (2011). Because melatonin is sparingly soluble at near neutral and basic pH, the melatonin in an orally-releasing dosage form might not be soluble enough to be available for absorption via the oral mucosa, especially the sublingual or buccal mucosa.

The compositions described here overcome this problem. They include melatonin in an oral mucosal delivery dosage form adapted to release the melatonin in the mouth where it can then be absorbed through the oral mucosa and an acidifying agent that imparts a low enough pH to the dosage form and the saliva in the vicinity of the dosage form to render the melatonin water soluble.

The compositions are formulated to deliver melatonin across the oral mucosa. The oral mucosa include, for example, the buccal mucosa and sublingual mucosa. Depending on the formulation, different examples of the composition may be targeted for buccal and/or sublingual delivery.

The sublingual mucosa is the most permeable oral mucus membrane and is an established route of oral administration. The buccal mucosa is less permeable than the sublingual mucosa, but is also an established route of oral administration. Some examples of sublingual and buccal dosage forms include, dissolving tablets, lozenges, candy, strips, and soft capsules. Respectively, sublingual and buccal dosage forms yield a high sublingual/buccal concentration of melatonin so that melatonin can be absorbed across the sublingual/buccal mucosa. Delivery of active ingredients via the sublingual or buccal mucosa is known to produce a rapid onset of action of the active ingredient and bypasses the gastrointestinal tract.

There are many different types of orally dissolving dosage forms for absorption of active ingredients by the oral mucosa. Some examples of the oral mucosal dosage forms include orally dissolving tablets, chewable tablets, dissolving granules, lozenges, strips, chewing gums, and the like. Although certain particular examples of these dosage forms are described herein, it should be understood that the scope of this disclosure includes preparing the composition in any of these dosage forms and like dosage forms that are not mentioned here in detail.

An orally dissolving tablet or an orally disintegrating tablet is formulated to disintegrate in the mouth rather than being swallowed whole. One of the advantages of such a dosage form is that it can be administered without water. Saliva from the subject's mouth causes the tablet to disintegrate. The disintegrated contents may be held in the subject's mouth without swallowing for a specified time while the melatonin absorbs into the subject's oral mucosa.

Orally dissolving tablets may be prepared by blending the ingredients together and compressing them into a tablet. The tablet may have any desired shape, but is often disc-shaped and is small enough to sit in a cavity in the mouth adjacent the oral mucosa being targeted for delivery.

A sublingual tablet is intended to be held under the tongue without swallowing for a time while the tablet disintegrates and the melatonin is absorbed through the sublingual mucosa. Accordingly, a sublingual tablet should have a size and shape that is comfortable for placement under the tongue.

A buccal tablet is intended to be held between the teeth and the cheek without swallowing for a time while the tablet disintegrates and the melatonin is absorbed through the buccal mucosa. Accordingly, a buccal tablet should have a size and shape that is comfortable for placement between the teeth and cheek.

The tablet, regardless of its intended target for absorption, may be placed directly onto the tongue where it can dissolve and the melatonin be absorbed through the oral mucosa generally.

In another example, the tablet is a chewable tablet that is chewed by the patient. The chewable tablet may be administered by placing it in the patient's mouth. The chewable tablet can then be moved around within the mouth during chewing. The chewed product can sometimes be packed between the gums and the cheeks or underneath the tongue.

A polymer strip, orally dissolving strip, or oral thin film dosage form is a thin polymer film, often less than 1 mm thick, that adheres to the skin inside the mouth and rapidly disintegrates thereon. The strip includes a hydrophilic polymer carrier matrix that contains the melatonin. The strip does not require water for administration since it will disintegrate on contact with saliva.

As compared to a tablet, the strip is flexible and requires less packaging space. The strip also provides a larger surface area for contacting the skin compared to tablets. The surface area may be, for example 1-20 cm$^2$.

The strip is intended to be placed on the skin inside the mouth, often on the tongue, under the tongue, or cheek, and held without swallowing for a time while the strip disintegrates and the melatonin is absorbed through the oral mucosa.

The polymer strip dosage form may be prepared using a conventional approach such as solvent casting, hot-melt extrusion, semisolid casting, sold dispersion extrusion, and rolling.

The composition may be formulated in such a way that the dosage form completely disintegrates within the mouth in about 15 minutes, about 10 minutes, about 5 minutes, about 3 minutes, about 2 minutes, or about 1 minute following administration to the mouth and contact with the saliva.

The acidifying agent lowers the pH inside the mouth to temporarily lower the local pH of the saliva and/or the tongue coating to maintain melatonin in a soluble form at the mucosa interfaces for absorption. The acidifying agent lowers the pH of saliva and/or the tongue coating to a pH of about 4 or less, about 1 to about 4, about 2 to about 4, or about 3 to about 4. The pH may be maintained at the desired level during substantially the entire time from when the composition begins to disintegrate in the saliva to when it is completely disintegrated in the saliva. In a particular example, the pH is maintained at 3.3 or below, which is below the pK$_a$ of melatonin.

The composition is configured to disintegrate in saliva and maintain a pH of 4 or less within the saliva during the time the dosage form is dissolving therein. In certain examples the pH is maintained at 3.3 or less or from 2 to 3.3. The phrase "during the time the dosage form is dissolving therein" refers to the time from when the dosage form has disintegrated enough in saliva to create a local pH within the desired range to make the melatonin in the dosage form soluble. The amount of acidifying agent in the composition is selected to provide the desired pH.

The acidifying agent may include at least one organic and/or inorganic acid, including carboxylic acids such as citric acid, succinic acid, tartaric acid, acetic acid, or the like; and phosphoric acid, hydrochloric acid, or the like.

The acidifying agent may include at least one buffering agent such as a conjugate base of the acid(s) used in the acidifying agent. Examples include citrate salts such as monosodium citrate, and phosphate salts such as phosphoric acid monopotassium salts, and the like.

The ingredients of the composition are combined in a carrier matrix that provides the physical structure of the dosage form. The composition of the carrier matrix will vary depending on the type of dosage form being used.

For tablet type dosage forms and the like, the majority of the carrier matrix may be a pharmaceutical filler or bulking agent. Examples of such fillers include, but are not limited to, sucrose, lactose, mannitol, dicalcium phosphate dihydrate, starch, cellulosic materials, microcrystalline cellulose, and the like.

For tablet type dosage forms and the like, carrier matrix may also include a disintegrant. The disintegrant is effective to speed the rate of disintegration of the dosage form in the mouth, often by swelling and causing the dosage form to fall apart. Some examples of disintegrants include, but are not limited to, croscarmellose sodium, crospovidone, sodium starch glycolate, and the like. The disintegrant may also be called a superdisintegrant.

The composition may include a binder that helps adhere the components of the dosage form together. Examples of binders include, but are not limited to, sugars such as glucose, lactose, dextrose, fructose, sucrose, and the like; sugar alcohols such as mannitol, sorbitol, and xylitol and the like; gums such as acacia gum, xanthan gum, guar gum, locust bean gum, and the like; starch; cellulose, microcrystalline cellulose, polyvinylpyrrolidone, alginate, gelatin, methylcellulose, ethylcellulose, carboxymethylcellulose, hydroxypropylmethylcellulose, polyacrylic acid, polyethylene glycol, and other possibilities.

For polymer strip type dosage forms, the carrier matrix may include a water soluble polymer. Examples of water soluble polymers include, but are not limited to, polyethylene oxide, maltodextrin, hydroxypropyl methylcellulose, hydroxypropyl cellulose, starch, modified starch, pullan, gelatin, carboxymethyl cellulose, and the like.

For polymer strip type dosage forms, the carrier matrix may also include a plasticizer, typically in an amount less than the polymer. The plasticizer is effective to soften the polymer and render it more flexible that it would otherwise be without the plasticizer. Examples of plasticizers include, but are not limited to, glycerol, glycerin, polyethylene glycols, propylene glycol, sorbitol sorbitan, and the like.

The composition may include a thickener. Examples of thickeners include, but are not limited to, gum bases, and the like, gums such as acacia gum, xanthan gum, guar gum, locust bean gum, carrageenan, and the like. A thickener may be especially useful in polymer strip dosage forms.

The composition may include a surfactant. Examples of surfactants include, but are not limited to, sodium lauryl sulfate, benzalkonium chloride, benzethonium chloride, polysorbate 20, cetearyl alcohol, glyceryl surfactants, cetyl pyridinium chloride, and the like.

The composition may include a mucoadhesive agent such as a mucoadhesive polymer to enhance adhesion of the dosage form to the oral mucosa, which might also improve retention at the desired delivery site. Examples of mucoadhesive agents include, but are not limited to, alginates, lectins, carageenans, pectins, cellulosic materials, and the like.

The composition may include a sweetener to enhance the taste of the dosage form. Sweeteners include both natural and artificial sweeteners including, but not limited to, sucralose, aspartame, saccharin, stevia, acesulfame potassium, sugar alcohols such as glycerol, sorbitol, maltitol, mannitol, and erythritol, isomalt, maltodextrin, natural sugars, and the like.

The composition may include a flavor such as a natural or artificial flavor. The composition may also include a coloring agent to give the dosage form a desirable color.

Several more particular examples of the composition will now be described. These examples are presented as percent by weight (% w/w) of the specified ingredient relative to the dosage form. Any combination of the ingredients in the % w/w listed below may be employed in any of the example compositions discussed herein.

In some of the compositions, melatonin may be 0.1%-5% w/w; 0.1%-2% w/w, 0.1% to 1% w/w, or 0.2%-0.7% w/w of the composition.

In some of the compositions, the acidifying agent may be 0.5%-30% w/w, 1%-25% w/w, 25%-30% w/w, 8%-12% w/w, 1%-15% w/w, 5%-15% w/w, 2%-10% w/w, 7%-15% w/w, 6%-40% w/w, or 7%-9% w/w of the composition. The amount of acidifying agent is effective to impart the pH discussed herein to the dosage form and saliva in the vicinity of the dosage to render melatonin soluble in the saliva.

Three more particular examples of possible dosage forms are now discussed. It should be understood that all three of these dosage form examples are examples of the first example of the composition discussed above.

TABLE 1

Examples of possible amounts of certain ingredients in a dosage form

| Ingredient | % w/w | % w/w | % w/w | % w/w |
|---|---|---|---|---|
| melatonin | 0.2-2 | 0.5-1.5 | 0.8-1.2 | about 1 |
| disintegrant | 15-20 | 16-19 | 16-18 | about 17.5 |
| acidifying agent | 20-30 | 22-29 | 25-29 | about 27.5 |
| filler | 46-63 | 50-60 | 52-58 | about 54 |

Table 1 provides several examples of exemplary % w/w ranges of certain primary ingredients in a dosage form such as a sublingual tablet. The % w/w balance of the dosage form of Table 1 may include a flow agent, a sweetener, a flavor, and a color, for example. The flow agent may be 0.05% w/w to 0.2% w/w or about 0.1% w/w of the dosage form. The flavor may be 0.1% w/w to 5% w/w or about 2.5% w/w of the dosage form. The sweetener may be 0.1% w/w to 5% w/w or about 2.5% w/w of the dosage form. The color may be 0.25% w/w to 0.75% w/w or about 0.5% w/w of the dosage form.

TABLE 2

Examples of possible amounts of certain ingredients in a dosage form

| Ingredient | % w/w | % w/w | % w/w | % w/w |
|---|---|---|---|---|
| melatonin | 0.2-2 | 0.5-1.5 | 0.8-1.2 | about 1 |
| disintegrant | 6-10 | 7-9 | 7.5-8.5 | about 8 |
| acidifying agent | 20-30 | 22-29 | 25-29 | about 27.5 |
| filler | 50-68 | 55-61 | 56-60 | about 58 |

Table 2 provides several examples of exemplary % w/w ranges of certain primary ingredients in a dosage form such as a buccal tablet. The % w/w balance of the dosage form of Table 2 may include a flow agent, a sweetener, a flavor, and a color, for example. The flow agent may be 0.05% w/w to 0.2% w/w or about 0.1% w/w of the dosage form. The flavor may be 0.1% w/w to 5% w/w or about 2.5% w/w of the dosage form. The sweetener may be 0.1% w/w to 5% w/w or about 2.5% w/w of the dosage form. The color may be 0.25% w/w to 0.75% w/w or about 0.5% w/w of the dosage form.

TABLE 3

Examples of possible amounts of certain ingredients in a dosage form

| Ingredient | % w/w | % w/w | % w/w | % w/w |
|---|---|---|---|---|
| melatonin | 0.05-2 | 0.25-1.5 | 0.25-0.75 | about 0.5 |
| carrier matrix polymer | 45-90 | 55-65 | 58-62 | about 60 |
| acidifying agent | 5-20 | 7-13 | 8-12 | about 10.5 |

Table 3 provides several examples of exemplary % w/w ranges of certain primary ingredients in a dosage form such as a polymer strip. The % w/w balance of the dosage form of Table 3 may include a plasticizer, a surfactant, a thickener, a sweetener, a flavor, and a color, for example. The plasticizer may be 1% w/w to 20% w/w or about 10% w/w of the dosage form. The surfactant may be % w/w to 20% w/w or about 10% w/w of the dosage form. The thickener may be 2.5% w/w to 5% w/w or about 3.5% w/w of the dosage form. The flavor may be 0.1% w/w to 5% w/w or about 2.5% w/w of the dosage form. The sweetener may be 0.1% w/w to 5% w/w or about 2.5% w/w of the dosage form. The color may be 0.25% w/w to 0.75% w/w or about 0.5% w/w of the dosage form.

For any of the examples presented in Tables 1-3 the specified ingredient may be, for example, one or more of the ingredients in each class discussed in previous paragraphs.

The composition may be administered orally to a human or animal patient in a therapeutically effective amount, which is an amount that is sufficient to provide a therapeutic benefit affecting a disease or condition in the body.

A therapeutically effective amount of melatonin may be, for example: 0.01-1,000 mg, 0.01-500 mg, 0.01-100 mg, 0.01 to 50 mg, 0.01-25 mg, 0.01-10 mg, 0.01-5 mg. The therapeutically effective amount can vary outside of these ranges as well. The weight in mg is often calibrated to the body weight of the patient in kg, thus these example doses may also be written in terms of mg/kg of body weight per day.

In practice, the therapeutically effective amount may vary depending on numerous factors associated with the patient, including age, weight, height, severity of the condition, administration technique, and other factors. The therapeutically effective amount administered to a patient may be determined by medical personnel taking into account the relevant circumstances.

The therapeutically effective amount may be determined or predicted from empirical evidence. Specific dosages may vary according to numerous factors and may be initially determined on the basis of experimentation.

The composition may be administered as a single dose or as part of a dosage regimen. For a dosage regimen, the therapeutically effective amount is adjustable dose to dose to provide a desired therapeutic response.

Multiple doses may be administered at a predetermined time interval and subsequent doses may be proportionally reduced or increased, depending on the situation.

The composition may be used to treat many physiological conditions for which melatonin provides a therapeutic benefit. In a particular method of use, the composition is used to provide an acute dose of melatonin to the patient at or near bedtime or when the patient awakes and desires to fall back asleep. The oral mucosal dosage form will provide a faster onset of melatonin's sleep aid effects compared to conventional melatonin dosage forms delivered through gastrointestinal tract.

An example method of treatment includes administering to a patient in need thereof a therapeutically effective composition including melatonin, a pharmaceutical carrier, and an amount of acidifying agent effective to lower the pH of a tongue coating to a pH of 4 or less. The composition may be administered by the patient, a physician, or the patient's caretaker by placing the composition in the patient's mouth and holding it in the mouth without swallowing the contents. In such a method, the composition is particularly advantageous for administration if the patient awakes in the middle of the night after being asleep and/or to help the patient initially fall asleep at bedtime. Administering may occur, for example, within 30 minutes of the time the subject desires to fall asleep and/or at night after the subject has awoken from sleep and desires to fall back asleep.

When administered, the composition is introduced to the patient's mouth and held in the mouth while the dosage form disintegrates. In some cases, the dosage form may be placed on top of the tongue while it disintegrates. In other cases it may be placed against the mucous membrane being targeted for delivery, such as the sublingual and/or buccal mucosa, and held there while it disintegrates.

EXAMPLES

The following examples are provided to illustrate aspects of certain examples of the composition. The scope of possible examples is not limited to the details of these examples.

Example 1

Tablet for Sublingual Delivery

Table 4 provides an example of a sublingual tablet dosage form and its ingredients in a particular example and a range of possible amounts in other possible examples.

TABLE 4

Sublingual tablet formulation

| Ingredient | Amount (mg/gm) | Range-Low (mg/gm) | Range-High (mg/gm) |
| --- | --- | --- | --- |
| Melatonin | 10 | .2 | 20 |
| disintegrant (e.g. croscarmellose sodium) | 175 | 150 | 200 |
| Citric acid | 275 | 200 | 300 |
| Filler/stabilizing agent (e.g. microcrystalline cellulose) | 539 | 460 | 630 |
| Flow agent (e.g. magnesium stearate) | 1 | .5 | 2 |
| Flavoring agents (e.g. menthol, lavender) | 25 | 1 | 50 |
| Sweetening agents (e.g. aspartame, sorbitol) | 25 | 1 | 50 |
| Coloring agents (e.g. titanium dioxide, FD&C coloring pigments) | 5 | 2.5 | 7.5 |
| TOTAL | 1000 | | |

The sublingual tablet is a small, flat tablet that is administered orally to be placed under the tongue. At which point, the tablet begins to disintegrate rapidly, allow the melatonin to be absorbed directly through the oral mucosa; bypassing first pass metabolism and being distributed directly into the venous blood supply.

The manufacture of the tablet in this example involves the dry blending and compression of the melatonin and excipients into a flat disc. The citric acid acts to control the pH to allow for transdermal delivery, and to stimulate saliva to help with dissolution and absorption. Other components include a high concentration of a disintegrant, a tablet filler, a powder flowing agent, as well as flavoring, sweetening and coloring agents.

Example 2

Tablet for Buccal Delivery

Table 5 provides an example of a buccal tablet dosage form and its ingredients in a particular example and a range of possible amounts in other possible examples.

TABLE 5

Buccal tablet formulation

| Ingredient | Amount (mg/gm) | Range-Low (mg/gm) | Range-High (mg/gm) |
| --- | --- | --- | --- |
| Melatonin | 10 | .2 | 20 |
| disintegrant (e.g. croscarmellose sodium) | 80 | 60 | 100 |
| Citric acid | 275 | 200 | 300 |
| Filler/stabilizing agent (e.g. microcrystalline cellulose) | 579 | 500 | 675 |
| Flow agent (e.g. magnesium stearate) | 1 | .5 | 2 |
| Flavoring agents (e.g. menthol, lavender) | 25 | 1 | 50 |
| Sweetening agents (e.g. aspartame, sorbitol) | 25 | 1 | 50 |
| Coloring agents (e.g. titanium dioxide, FD&C coloring pigments) | 5 | 2.5 | 7.5 |
| TOTAL | 1000 | | |

A buccal tablet is a small, flat tablet that is administered orally to be placed between the check and the gums (buccal cavity). At which point, the tablet begins to disintegrate rapidly, allow the melatonin to be absorbed directly through the buccal mucosa; bypassing first pass metabolism and being distributed directly into the venous blood supply.

The manufacture of the tablet in this example involves the dry blending and compression of the melatonin and excipients into a flat disc. The citric acid acts to control the pH to allow for transdermal delivery, and to stimulate saliva to help with dissolution and absorption. Other components include a disintegrant, a tablet filler agent, a powder flowing agent, as well as flavoring, sweetening and coloring agents.

Example 3

Oral Thin Film

Table 6 provides an example of a polymer strip or oral thin film dosage form and its ingredients in a particular example and a range of possible amounts in other possible examples.

TABLE 6

Polymer strip formulation

| Ingredient | Amount (mg/gm) | Range-Low (mg/gm) | Range-High (mg/gm) |
|---|---|---|---|
| Melatonin | 5 | 0.5 | 20 |
| Water soluble polymer (e.g. polyethylene oxide, maltodextrin, hydroxy propyl methyl cellulose, hydroxy propyl cellulose, starch or modified starch, pullulan, gelatin, carboxy methyl cellulose) | 600 | 450 | 900 |
| Plasticizer (e.g. glycerol, propylene glycol) | 100 | 10 | 200 |
| Citric acid | 105 | 50 | 200 |
| Stabilizing/thickening agents (e.g. xanthan gum, locust bean gum, carragenan) | 35 | 25 | 50 |
| Surfactant (e.g. sodium lauryl sulfate, benzalkonium chloride, benzthonium chloride, tween) | 100 | 10 | 200 |
| Flavoring agents (e.g. menthol, lavender) | 25 | 1 | 50 |
| Sweetening agents (e.g. aspartame, sorbitol) | 25 | 1 | 50 |
| Coloring agents (e.g. titanium dioxide, FD&C coloring pigments) | 5 | 2.5 | 7.5 |
| TOTAL | 1000 | | |

A polymer strip is a thin strip that is designed to disintegrate quickly under the tongue. Similar to the sublingual tablet, it is absorbed directly through the oral mucosa; bypassing first pass metabolism and being distributed directly into the venous blood supply.

The manufacture of this film is by hot melt extrusion. In this process, the solid materials including melatonin and excipients are loaded into a hopper, conveyed, mixed and melted by a ram or screw extruder. The extrudate is then deposited into a die of desirable form.

The citric acid acts to control the pH to allow for transdermal delivery, and to stimulate saliva to help with dissolution and absorption. Other components include water soluble polymer to act as the bulk of the film, a plasticizer to allow for film flexibility, a stabilizing agent, a surfactant, a flavoring agent, a sweetening agent, and a coloring agent.

This disclosure has described example embodiments, but not all possible embodiments of the compositions or associated methods. Where a particular feature is disclosed in the context of a particular example embodiment, that feature can also be used, to the extent possible, in combination with and/or in the context of other embodiments. The composition and related methods may be embodied in many different forms and should not be construed as limited to only the examples described here.

The compositions and methods are not limited only to the details described in connection with the example embodiments. There are numerous variations and modification of the compositions and methods that may be made without departing from the scope of what is claimed.

That which is claimed is:

1. A composition comprising a pharmaceutical tablet dosage form configured to disintegrate in oral saliva and maintain a pH of 4 or less within the saliva during the time the dosage form is dissolving therein, the dosage form including a therapeutically effective amount of melatonin in a carrier matrix, a disintegrant, and a sufficient amount of acid to impart the pH to the saliva, the amount of disintegrant being sufficient to cause the dosage form to completely disintegrate in the saliva within ten minutes from contacting the saliva, wherein the dosage form is a chewable tablet.

2. The composition of claim 1, wherein the pH is 2 to 4.

3. The composition of claim 1, wherein the disintegrant is 6% w/w to 20% w/w of the dosage form.

4. The composition of claim 1, wherein the acid is 20% w/w to 30% w/w of the dosage form.

5. The composition of claim 1, wherein the therapeutically effective amount of melatonin is 0.2 mg to 20 mg.

6. The composition of claim 1, wherein the carrier matrix includes microcrystalline cellulose which is 45% w/w to 68% w/w of the dosage form, the acid which is 20% w/w to 30% w/w of the dosage form, and the disintegrant which is 6% w/w to 20% w/w of the dosage form.

7. The composition of claim 1, wherein the acid is a carboxylic acid.

8. The composition of claim 1, wherein the acid is citric acid.

9. The composition of claim 1, wherein the amount of disintegrant is sufficient to cause the dosage form to completely disintegrate in the saliva within 2 minutes from contacting the saliva.

10. A method comprising administering a composition comprising a pharmaceutical tablet dosage form to a subject in need thereof, the dosage form dissolving in the subject's saliva while maintaining a pH of 4 or less within the saliva during the time the dosage form is dissolving, the dosage form including a therapeutically effective amount of melatonin in a carrier matrix, a disintegrant, and a sufficient amount of acid to impart the pH to the saliva, the amount of disintegrant being sufficient to cause the dosage form to completely disintegrate in the saliva within ten minutes from contacting the saliva, wherein the dosage form is a chewable tablet.

11. The method of claim 10, wherein the pH is 2 to 4.

12. The method of claim 10, wherein the disintegrant is 6% w/w to 20% w/w of the dosage form.

13. The method of claim 10, wherein the acid is 20% w/w to 30% w/w of the dosage form.

14. The method of claim 10, wherein the therapeutically effective amount of melatonin is 0.2 mg to 20 mg.

15. The method of claim 10, wherein the carrier matrix includes microcrystalline cellulose which is 45% w/w to 68% w/w of the dosage form, the acid which is 20% w/w to 30% w/w of the dosage form, and the disintegrant which is 6% w/w to 20% w/w of the dosage form.

16. The method of claim 10, wherein the acid is a carboxylic acid.

17. The method of claim 10, wherein the acid is citric acid.

18. The method of claim 10, wherein the amount of disintegrant is sufficient to cause the dosage form to completely disintegrate in the saliva within 2 minutes from contacting the saliva.

19. The method of claim 10, wherein administering occurs within 30 minutes of the time the subject desires to fall asleep.

20. The method of claim 10, wherein administering occurs at night after the subject has awoken from sleep and desires to fall back asleep.

21. The method of claim 10, wherein the acid is a carboxylic acid.

22. The method of claim 10, wherein the acid is citric acid.

23. A composition comprising:
a pharmaceutical tablet dosage form configured to disintegrate in saliva and maintain a pH of 4 or less within the saliva during the time the dosage form is dissolving therein, the dosage form including:
0.2% w/w to 20% w/w melatonin in a therapeutically effective amount;
a carrier matrix including 45% w/w to 68% w/w filler, 6% w/w to 20% w/w disintegrant, the amount of disintegrant being sufficient to cause the dosage form to completely disintegrate in the saliva within ten minutes from contacting the saliva; and 20% w/w to 30% w/w acid, the acid being effective to impart the pH, and wherein the dosage form is a chewable tablet to the saliva.

24. The composition of claim 23 wherein, the dosage form is a buccal or sublingual tablet.

25. The composition of claim 23, wherein the pH is 2 to 4.

26. The composition of claim 23, wherein the disintegrant includes crospovidone, the filler includes microcrystalline cellulose, and the acid includes citric acid.

27. The composition of claim 23, wherein the therapeutically effective amount of melatonin is 0.2 mg to 20 mg.

28. The composition of claim 23, wherein the acid is a carboxylic acid.

29. The composition of claim 23, wherein the acid is citric acid.

30. The composition of claim 23, wherein the amount of disintegrant is sufficient to cause the dosage form to completely disintegrate in the saliva within 2 minutes from contacting the saliva.

* * * * *

UNITED STATES PATENT AND TRADEMARK OFFICE
CERTIFICATE OF CORRECTION

PATENT NO. : 11,224,657 B2
APPLICATION NO. : 15/931029
DATED : January 18, 2022
INVENTOR(S) : Shah et al.

It is certified that error appears in the above-identified patent and that said Letters Patent is hereby corrected as shown below:

In the Claims

In Claim 23, (Column 13, Line 11) should read as follows:
23. A composition comprising: a pharmaceutical tablet dosage form configured to disintegrate in saliva and maintain a pH of 4 or less within the saliva during the time the dosage form is dissolving therein, the dosage form including: 0.2% w/w to 20% w/w melatonin in a therapeutically effective amount; a carrier matrix including 45% w/w to 68% w/w filler, 6% w/w to 20% w/w disintegrant, the amount of disintegrant being sufficient to cause the dosage form to completely disintegrate in the saliva within ten minutes from contacting the saliva; and 20% w/w to 30% w/w acid, the acid being effective to impart the pH to the saliva, and wherein the dosage form is a chewable tablet.

Signed and Sealed this
Third Day of May, 2022

Katherine Kelly Vidal
*Director of the United States Patent and Trademark Office*